US00PP32397P2

(12) United States Plant Patent
Zhang et al.

(10) Patent No.: US PP32,397 P2
(45) Date of Patent: Oct. 27, 2020

(54) ***NANDINA* PLANT NAMED 'ZHNAN28'**

(50) Latin Name: *Nandina domestica*
Varietal Denomination: ZhNan28

(71) Applicant: University of Georgia Research Foundation, Inc., Athens, GA (US)

(72) Inventors: Donglin Zhang, Watkinsville, GA (US); Matthew Dirr, Watkinsville, GA (US); Jinying Dong, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/602,885

(22) Filed: Dec. 18, 2019

(51) Int. Cl.
*A01H 5/00* (2018.01)
*A01H 6/00* (2018.01)

(52) U.S. Cl.
USPC ..... Plt./235
CPC ..... *A01H 6/00* (2018.05)

(58) Field of Classification Search
USPC ..... Plt./235
CPC ..... A01H 5/02; A01H 5/00; A01H 5/12
See application file for complete search history.

*Primary Examiner* — Kent L Bell
(74) *Attorney, Agent, or Firm* — Thomas|Horstemeyer, LLP

(57) ABSTRACT

A new and distinct cultivar of *Nandina* plant named 'ZhNan28', characterized by a combination of compact growing form, dense foliage, orange red (apricot) fall foliage persistent to 6 months, no seed, and no notable disease and pest.

3 Drawing Sheets

Figure 1:
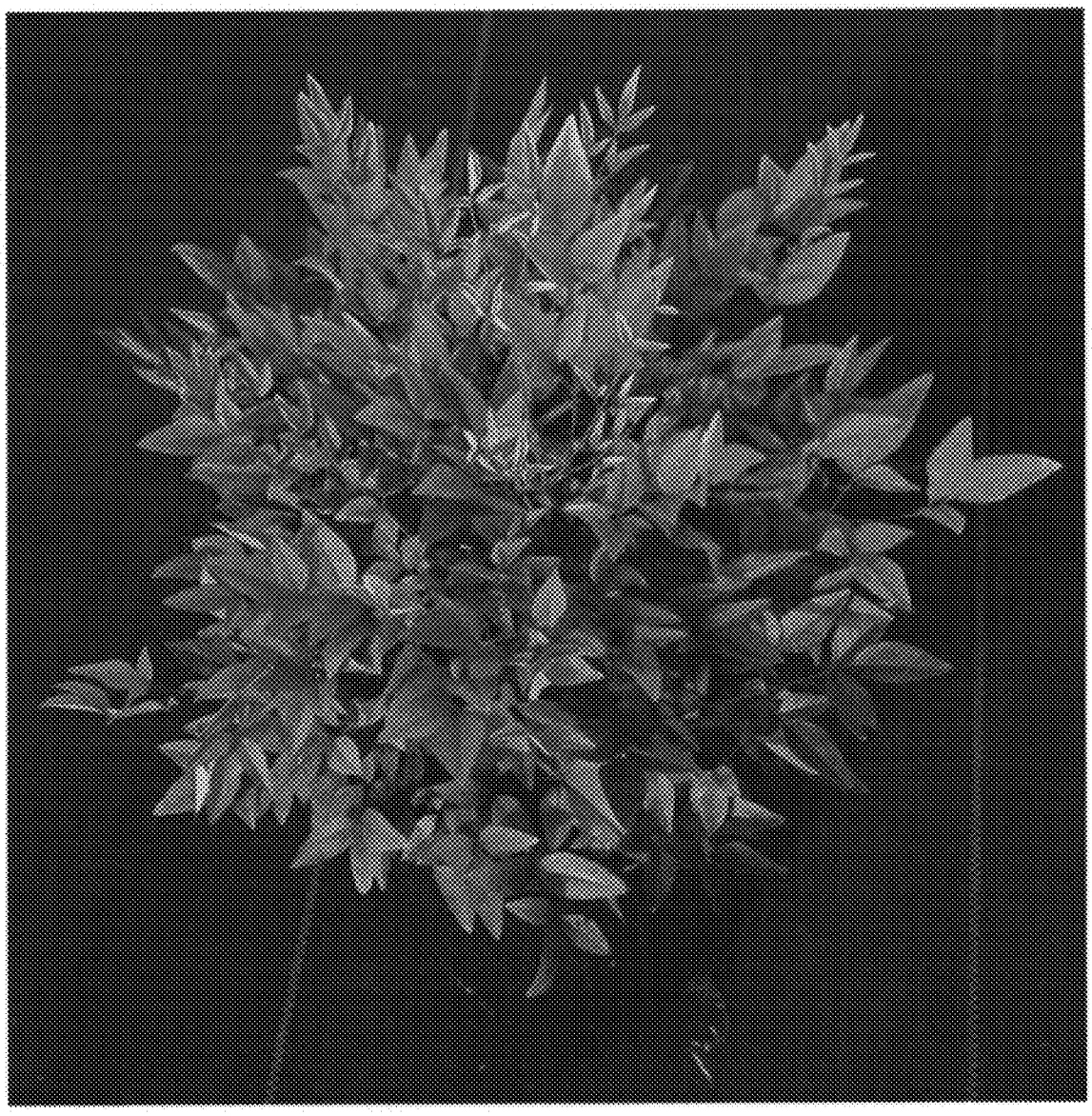

Botanical designation: *Nandina domestica.*
Cultivar denomination 'ZhNan28'.

BACKGROUND OF THE INVENTION

The present invention relates to a new and distinct cultivar of *Nandina*, botanically know as *Nandina domestica*, and hereinafter referred to by the cultivar name 'ZhNan28'.

The new *Nandina domestica* 'ZhNan28' is a product of a planned breeding program conducted by the inventors at a horticulture farm in Watkinsville, Ga. The objective of the *Nandina* breeding is to create new plant cultivars with compact habit, bright and colorful foliage, and less seed-bearing characteristics.

The new *Nandina domestica* 'ZhNan28' is a product of a selection from open pollinated seedling population. Seeds were collected on Sep. 23, 2012 from six compact-growing plants labeled as '*Nandina*01-02' to '*Nandina*06-02' (all 6 plants were not patented) at the horticulture farm in Watkinsville, Ga. and directly saw them into the germination flat. A total of 1108 germinated seedlings were transplanted into one-gallon containers on Mar. 11, 2013 for evaluation. On Oct. 8, 2014, seedlings without compact growing habit were discarded and 644 seedlings were grown on the nursery area for further evaluation as red, yellow and apricot foliage groups. Five plants from apricot foliage group were selected for further evaluation and *Nandina domestica* 'ZhNan28' was finally selected on Dec. 8, 2015.

Asexual reproduction of the new *Nandina domestica* 'ZhNan28' using vegetative terminal cuttings and tissue culture in controlled environment has been continued in Watkinsville, Ga. since 2014. Observations of the resulting 'ZhNan28' progeny have shown that the unique features of this new *Nandina domestica* 'ZhNan28' are stable and reproduced true to type in successive generations.

SUMMARY OF THE INVENTION

The new *Nandina* cultivar 'ZhNan28' has not been observed under all possible environmental conditions. The phenotype may vary somewhat with variations in environment and cultural practices such as water and light intensity without, however, any variance in genotype.

The following traits have been repeatedly observed and are determined to be the unique and distinguishing characteristics of the new *Nandina domestica* cultivar named 'ZhNan28'. In combination, these traits set 'ZhNan28' apart from all other existing varieties of *Nandina domestica* known to the inventors.

1. Compact growing form.
2. Dense foliage.
3. Orange red (apricot) fall foliage.
4. Orange red (apricot) foliage persistent to 6 months
5. No flower and seed observed.
6. No notable disease and pest.

Plants of the new *Nandina* differ from plants of *Nandina domestica* cultivar 'Gulf Stream' (U.S. Plant Pat. No. 5,656) in the following characteristics:

1. Plants of the new *Nandina* exhibit orange red (apricot) fall foliage.
2. Plants of the new *Nandina* are extremely compact, with tighter branches and denser foliage.

BRIEF DESCRIPTION OF THE PHOTOGRAPHS

The accompanying colored photographic illustrations show the overall appearance and distinct characteristics of the new cultivar of *Nandina domestica* 'ZhNan28' showing the colors as true as possible. Colors in the photographs may differ slightly from the color values cited in the detailed botanical description, which accurately describes the colors of the new *Nandina domestica* 'ZhNan28'. The photographs were taken of plants grown outdoors in Watkinsville, Ga. on Jan. 6, 2016.

The photograph labeled FIG. 1 depicts a top view of a typical 3-year-old 'ZhNan28' plant showing the orange red foliage.

Figure 2:
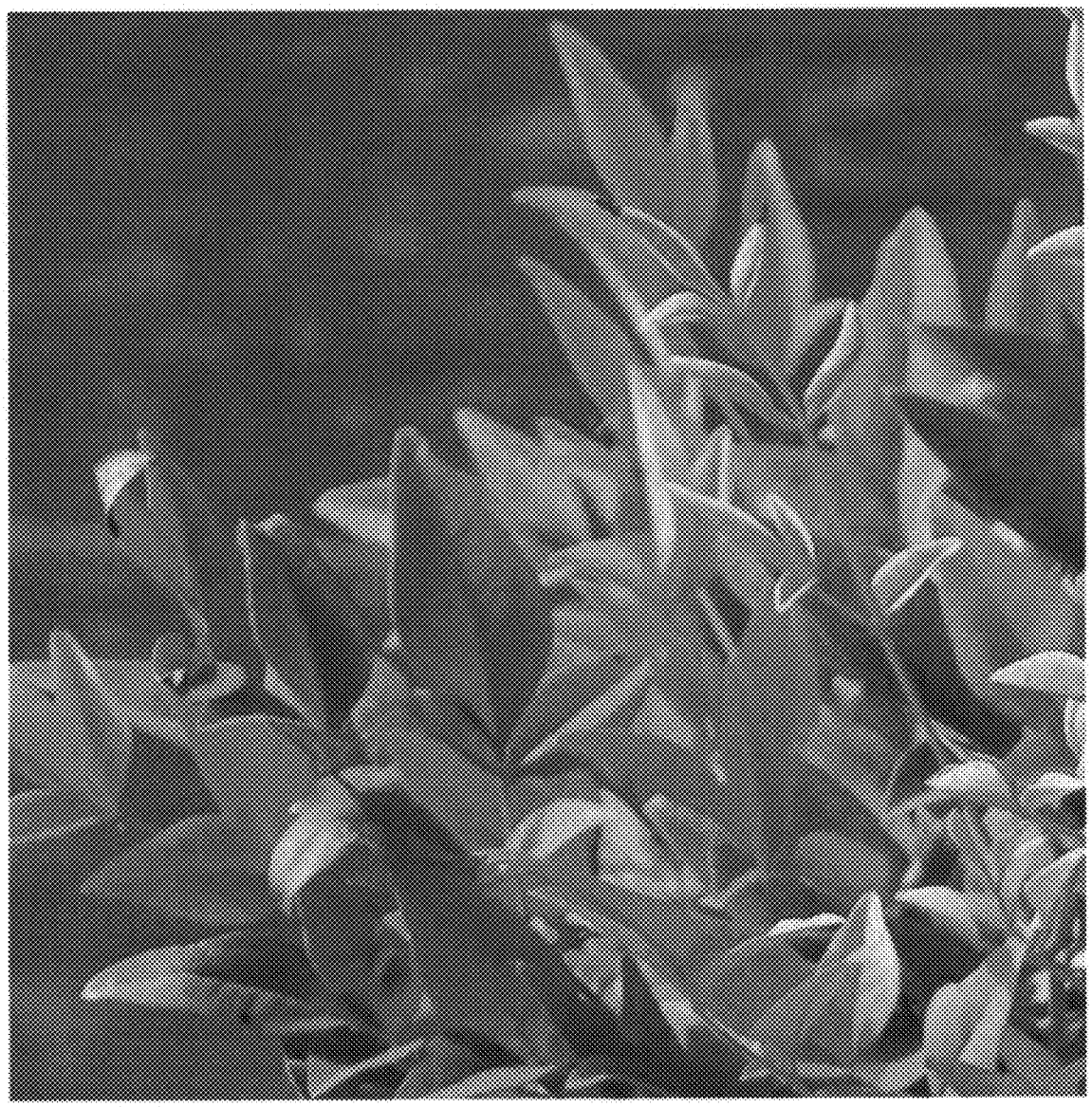

The photograph labeled FIG. 2 depicts a close-up view of the leaves of a typical 3-year-old 'ZhNan28' plant showing the orange red foliage.

Figure 3:
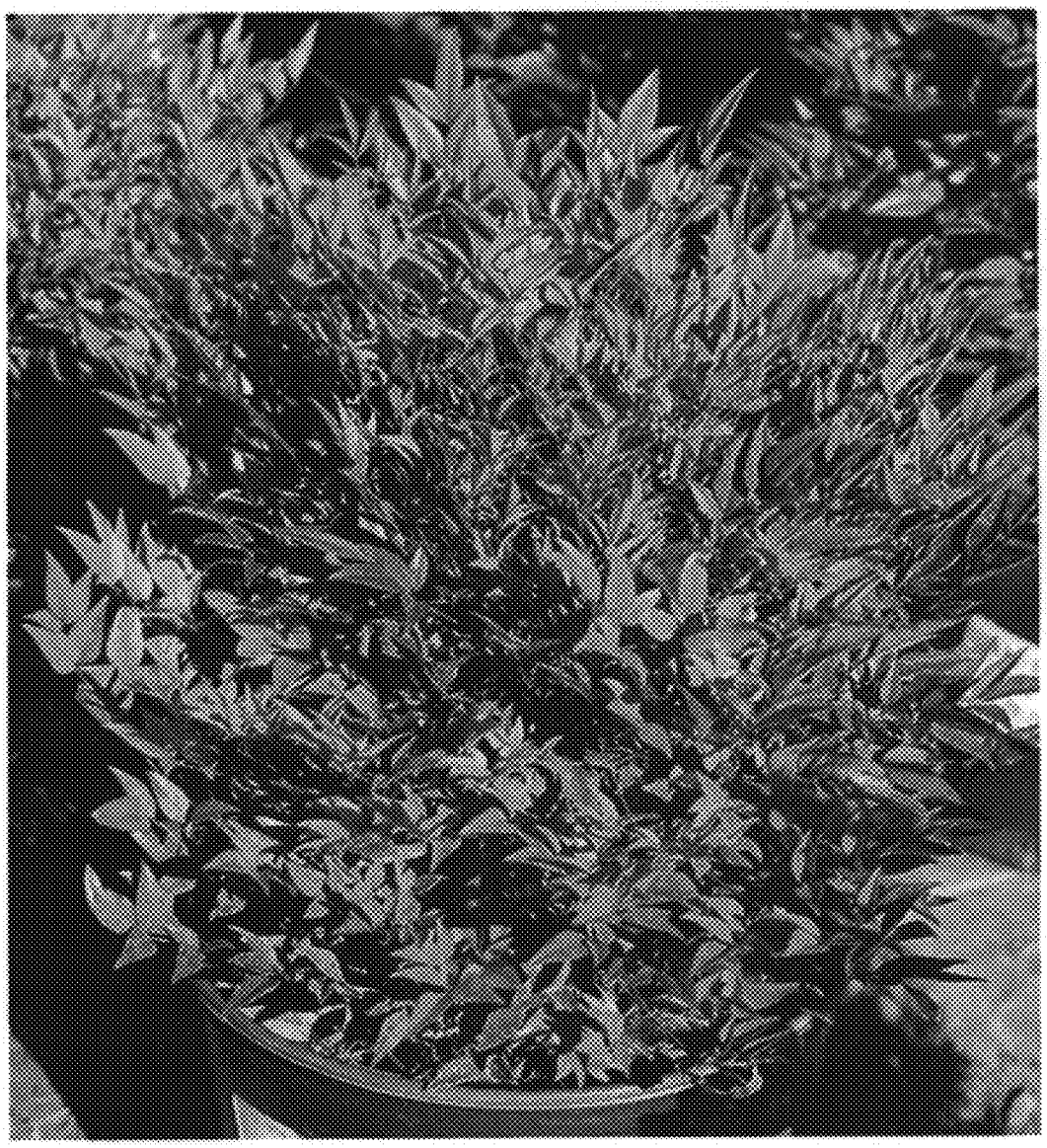

The photograph labeled FIG. 3 depicts a side view of a typical 3-year-old 'ZhNan28' plant showing the orange red foliage.

DETAILED BOTANICAL DESCRIPTION

The aforementioned photographs and following observations, measurements, and values describe plants of the *Nandina domestica* cultivar named 'ZhNan28'. Data were collected from a horticulture farm and nursery in Watkinsville, Ga. from 3-year-old plants (planted into 3-gallon container). The average low temperatures ranged from about 22-23° F. to 67-68° F. in the winter and about 66-67° F. to 97-98° F. in summer. The data below were collected on Jan. 6, 2016. Color names and values are from The R.H.S. Colour Chart, 5$^{th}$ edition, published by The Royal Horticultural Society (R.H.S.), London, UK in 2007, except where general terms of ordinary dictionary significance are used.

Botanical classification: *Nandina domestica* 'ZhNan28'.

Commercial classification: Shrub.

Parentage: Open pollination/seed propagation of six *Nandina domestica* cultivars '*Nandina*01-02', '*Nandina*02-02', '*Nandina*03-02', '*Nandina*04-02', '*Nandina*05-02', and '*Nandina*06-02', none of which are patented.

Growth and propagation:

*Propagation type*.—By terminal vegetative cuttings and tissue culture.

*Growth rate*.—Hardwood cuttings rooted in 3-5 weeks at an approximate temperature of 75° F. under the mist.

*Root description*.—White fibrous roots, initiated at the portion under the media.

*Rooting habit*.—Dense, health, freely branching root system.

Plant description:

*Form*.—Evergreen shrub, upright with densely foliated, round or very short columnar.

*Branching habit*.—Upright, compact.

*Usage*.—Various uses, such as container patio plants, potted plants, border, hedge, and mass planting.

*Vigor*.—Vigorous in the first and second years, then slowly.

*Size of plant*.—A. Height (cm): About 23.3 cm. B. Plant diameter and area of spread (diameter of the canopy): About 33.4 cm.

*Stem*.—A. Color: 1. Upper: 73B. 2. Lower: N187B. B. Length: About 23.3 cm. C. Base Diameter: About 6.8 mm. D. Pubescence: None. E. Shape: Rounded. F: Odor (of bruised stem): None. G. Internode length: about 3 mm, covered by petiole sheath. H: Description: Stem completely covered by foliage, not showy. I: Texture and Strength, mature: Very strong woody stems, a few upright later branching, which significantly increased plant density and foliage covering.

*Leaf*.—A. Leaf type: Bi- or tri-pinnately compound. B. Mature size (L×W): About 22.4×about 16.4 cm. C. Arrangement on stem: Alternate. D. Leaf number: Average of about 10 to about 17 per lateral branch.

*Leaflet*.—A. Color (R.H.S.): 1. Fall-Winter: Predominately 31A on both sides. 2. Spring-Summer: Predominately 137B (upper) and 138C (lower). B. Mature size (L×W): About 2.58×about 0.85 cm. C. Leaflet Number: Average of about 41 to about 77 per leaf. D. Apex: Acuminate. E. Base: Cuneate. F. Margin: Entire. G. Shape: Lanceolate. H. Number of lobes: None. I. Pubescence: None (glabrous). J. Venation: Netted (reticulate). K. Texture: Leathery, smooth on both sides.

*Petiole*.—A. Length: About 1.9 cm. B. Shape: rounded. C. Colour (R.H.S.): 1. Fall/Winter: 64A. 2. Summer: 148B. D. Pubescence: None. E. Diameter: About 2.3 mm. F. Sheath: Semi-sheath about 1 cm long, covered stem to about ⅔.

*Flower*.—None.

*Fruit*.—None.

*Seed*.—None.

Weather/temperature tolerance: Plants of the new *Nandina* have been observed to tolerate temperatures from about 11° F. to about 104° F. and have been observed to be very tolerant to drought and full sun conditions.

Disease/pest resistance: Plants of the new *Nandina* have been observed to be resistant to diseases and pests common to *Nandina*.

It is claimed:

1. A new and distinct cultivar of the *Nandina* plant named 'ZhNan28' as illustrated and described herein.

* * * * *